US012565635B2

(12) United States Patent     (10) Patent No.:   US 12,565,635 B2

Bhargav et al.     (45) Date of Patent:     Mar. 3, 2026

(54) METHOD OF OPERATION OF A PERFUSION SYSTEM

(71) Applicant: Cytiva Sweden AB, Uppsala (SE)

(72) Inventors: Anoop Bhargav, Bangalore Karnataka (IN); Praveen Paul, Bangalore Karnataka (IN); Prashanth Hosabettu Mohan, Bangalore Karnataka (IN); Ajay Gore, Bangalore Karnataka (IN); Pradeep Kumar, Bangalore Karnataka (IN); Victor Jose, Bangalore Karnataka (IN); Sahebagouda Alagur, Bangalore Karnataka (IN); Melissa Marie Semple, Marlborough, MA (US); Mark David Roberts, Marlborough, MA (US)

(73) Assignee: Cytiva Sweden AB, Uppsala (SE)

( * ) Notice: Subject to any disclaimer, the term of this patent is extended or adjusted under 35 U.S.C. 154(b) by 927 days.

(21) Appl. No.: 17/268,486

(22) PCT Filed: Aug. 20, 2019

(86) PCT No.: PCT/EP2019/072244

§ 371 (c)(1),
(2) Date: Feb. 15, 2021

(87) PCT Pub. No.: WO2020/043550

PCT Pub. Date: Mar. 5, 2020

(65) Prior Publication Data

US 2021/0261900 A1     Aug. 26, 2021

(30) Foreign Application Priority Data

Aug. 29, 2018    (IN) ............................. 201841032297

(51) Int. Cl.
    B01D 61/10      (2006.01)
    B01D 61/20      (2006.01)
      (Continued)

(52) U.S. Cl.
    CPC ............. C12M 33/14 (2013.01); B01D 61/10 (2013.01); B01D 61/20 (2013.01); B01D 65/02 (2013.01);
      (Continued)

(58) Field of Classification Search
    CPC ...... C12M 33/14; C12M 29/04; C12M 29/10; C12M 41/40; C12M 47/10; C12M 41/00;
      (Continued)

(56) References Cited

U.S. PATENT DOCUMENTS 6,755,970 B1 *   6/2004   Knappe .................. B01D 65/02
                                        210/321.74
2008/0179244 A1 *   7/2008   Morgan .................. B01D 65/02
                                        210/636

(Continued)

FOREIGN PATENT DOCUMENTS

WO     2015/039115 A1    3/2015
WO     2017/029305 A1    2/2017

(Continued)

OTHER PUBLICATIONS

Examination Report Issued in India Patent Application No. 202017049902, mailed Sep. 12, 2022. (5 pages with English Translation).

(Continued)

*Primary Examiner* — Hayden Brewster

(74) *Attorney, Agent, or Firm* — Eversheds-Sutherland (US) LLP

(57) ABSTRACT

A method includes inducing a first quantity of a feed fluid (28) to flow along a first direction (72) from a bioreactor (12) to a tangential flow filter (16) to separate the first quantity of the feed fluid (28) into a permeate fluid (42) and a retentate fluid (48). Further, the control unit (66) is operated to control at least one feed flow control device (24, 26) to inhibit the (Continued)

flow of first quantity of the feed fluid (28). Furthermore, the control unit (66) is operated to control the at least one feed flow control device (24, 26) to direct at least one of further flow of a second quantity of the feed fluid (28) from the bioreactor (12), a portion of the permeate fluid (42), and a portion of a nutrient fluid, along a second direction (74) opposite to the first direction (72) via the tangential flow filter (16).

16 Claims, 5 Drawing Sheets

(51) Int. Cl.
 *B01D 65/02* (2006.01)
 *C12M 1/00* (2006.01)
 *C12M 1/26* (2006.01)
 *C12M 1/34* (2006.01)
(52) U.S. Cl.
 CPC ............ *C12M 29/04* (2013.01); *C12M 29/10* (2013.01); *C12M 41/40* (2013.01); *C12M 47/10* (2013.01); *B01D 2315/10* (2013.01); *B01D 2321/12* (2013.01); *B01D 2321/40* (2013.01)
(58) Field of Classification Search
 CPC ........ B01D 61/10; B01D 61/20; B01D 65/02; B01D 2315/10; B01D 2321/12; B01D 2321/40; B01D 61/02; B01D 61/14; B01D 2321/04
 See application file for complete search history.

(56) References Cited

U.S. PATENT DOCUMENTS

| | | | |
|---|---|---|---|
| 2013/0157353 A1* | 6/2013 | Dijkhuizen Borgart | .................... C12M 29/04 435/297.1 |
| 2014/0356849 A1* | 12/2014 | Wikswo | ............. G01N 33/5005 435/284.1 |
| 2015/0039115 A1* | 2/2015 | Sagara | ............. G05B 19/41865 700/106 |
| 2015/0158907 A1* | 6/2015 | Zhou | ...................... C12M 47/10 530/399 |
| 2015/0247114 A1* | 9/2015 | Gebauer | ................ C12M 41/00 435/243 |
| 2016/0059160 A1* | 3/2016 | Steen | ................... B01D 61/145 210/788 |
| 2020/0318060 A1* | 10/2020 | Castillo | .................. C12M 29/10 |

FOREIGN PATENT DOCUMENTS

| | | | | |
|---|---|---|---|---|
| WO | WO-2018015386 A1 * | 1/2018 | ............ | C12M 21/00 |
| WO | WO-2020081344 A1 * | 4/2020 | | |

OTHER PUBLICATIONS

PCT International Search Report and Written Opinion for PCT/EP2019/072244 mailed Nov. 27, 2019 (9 pages).

* cited by examiner

METHOD OF OPERATION OF A PERFUSION SYSTEM

CROSS REFERENCE TO RELATED APPLICATIONS

This application claims the priority benefit of PCT/EP2019/072244, filed on Aug. 20, 2019, which claims the benefit of Indian Application No. 201841032297, filed on Aug. 29, 2018, the entire contents of which are incorporated by reference herein.

FIELD OF INVENTION

The embodiments of the present specification relate generally to filtration systems, and more particularly, to a perfusion system having a tangential flow filter and a method for cleaning the tangential flow filter of the perfusion system.

BACKGROUND OF INVENTION

Existence of many substances as solutions or mixtures created a need for processes to be developed to separate the solutions or mixtures. The need to purify, recover, isolate, and remove substances in process streams in chemical, pharmaceutical, food, petroleum, healthcare, and waste water applications has driven the need for separation technology.

The most common filtration processes are microfiltration (MF), ultrafiltration (UF), and reverse osmosis (RO). Such filtration processes are pressure driven and are used for separation of macromolecules from a fluid using a filter. The filter serves as a selective barrier by permitting certain constituents of a mixture to passthrough while retaining other constituents of the mixture. The filtration process results in two phases, permeate and retentate phases.

For a bioprocessing application, continuous processing is a growing trend because a smaller bioreactor can be used to produce a required quantity of a product compared to use of a larger bioreactor operated in fed batch mode. Perfusion enables continuous processing by enabling continuous nutrient supply and waste removal. The continuous process results in better product yield, product quality, process intensification, reduced capex, and reduced operation expenditure.

A drawback associated with use of filter separation process is a phenomenon known as fouling of the filter. Fouling is the deposition of material, referred to as foulant, on a surface of the membrane or pores of the filter, leading to a change in filter performance or even complete plugging of the filter. As a result, filter efficiency reduces due to the filter clogging, which in turn impacts filtration quality and increases overall processing time. In scenarios where a single use tangential flow filter is used for continuous processing, filter clogging restricts a duration for which the process can be run without interruption. Specifically, filter clogging restricts a duration of perfusion and limits a cell density that can be achieved at the end of the process.

There is a need for an enhanced perfusion system having a tangential flow filter and a method for cleaning the tangential flow filter of the perfusion system.

BRIEF DESCRIPTION OF INVENTION

In accordance with one aspect of the present specification, a method of operation of a system is disclosed. The method includes inducing a first quantity of a feed fluid to flow along a first direction from a bioreactor to a tangential flow filter via a feed flow path. The method further includes controlling at least one feed flow control device in the feed flow path, by a control unit, for controlling said flow and as a result of said flow along said first direction, allowing the tangential flow filter to separate the first quantity of the feed fluid into a permeate fluid and a retentate fluid. Furthermore, the method includes operating the control unit to control the at least one feed flow control device to inhibit or stop the flow of the first quantity of the feed fluid. Additionally, the method includes operating the control unit to control the at least one feed flow control device to direct at least one of a) a further flow of a second quantity of the feed fluid from the bioreactor, b) a portion of the permeate fluid, and c) a portion of a nutrient fluid from a source, along a second direction opposite to the first direction via the tangential flow filter for a predefined duration to clean the tangential flow filter.

In accordance with one aspect of the present specification, a system is disclosed. The system includes a bioreactor and a tangential flow filter coupled to the bioreactor via a feed flow path and at least one feed flow control device. The tangential flow filter is used to separate a feed fluid to a permeate fluid and a retentate fluid. The system further includes a control unit communicatively coupled to the at least one flow control device. The control unit is configured to induce a first quantity of a feed fluid to flow along a first direction from a bioreactor to a tangential flow filter via a feed flow path. The control unit is further configured to control at least one feed flow control device in the feed flow path for controlling said flow. Furthermore, the control unit is configured to control the at least one feed flow control device to inhibit or stop the flow of the first quantity of the feed fluid. Additionally, the control is configured to control the at least one feed flow control device to direct at least one of a) a further flow of a second quantity of the feed fluid from the bioreactor, b) a portion of the permeate fluid, and c) a portion of a nutrient fluid from a source, along a second direction opposite to the first direction via the tangential flow filter for a predefined duration to clean the tangential flow filter.

BRIEF DESCRIPTION OF DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "first," "second," and the like, as used herein do not denote any order, quantity, or importance, but rather are used to distinguish one element from another. Also, the terms "a" and "an" do not denote a limitation of quantity, but rather denote the presence of at least one of the referenced items. The use of "including," "comprising", or "having" and variations thereof herein are meant to encompass the items listed thereafter and equivalents thereof as well as additional items. The terms "communicatively coupled" and "coupled" are not restricted to physical or mechanical connections or couplings, and can include electrical connections or wireless couplings, whether direct or indirect.

In accordance with an embodiment of the present specification, a method is disclosed. The method includes inducing a first quantity of a feed fluid to flow along a first direction from a bioreactor to a tangential flow filter via a feed flow path. The method further includes controlling at least one feed flow control device in the feed flow path, by a control unit, for controlling said flow. Furthermore, the method includes allowing the tangential flow filter to separate the first quantity of the feed fluid into a permeate fluid and a retentate fluid. The method further includes operating the control unit to control the at least one feed flow control device to inhibit or stop the flow of the first quantity of the feed fluid. Additionally, the method includes operating the control unit to control the at least one feed flow control device to direct at least one of a) a further flow of a second quantity of the feed fluid from the bioreactor, b) a portion of the permeate fluid, and c) a portion of a nutrient fluid from a source, along a second direction opposite to the first direction via the tangential flow filter for a predefined duration to clean the tangential flow filter.

In accordance with another embodiment, an associated system is disclosed. In accordance with the embodiments of the present specification, the exemplary system and method enable to reduce filter clogging, thereby permitting intensification of a bioprocess and to increase a life of the tangential flow filter. The entire filter cleaning process is completely sterile and automatic since there is no requirement for an intervention of a user. Furthermore, it is possible to generate higher density cell cultures since the cleaning of the filter can be performed during the bioprocess.

Figure 1:
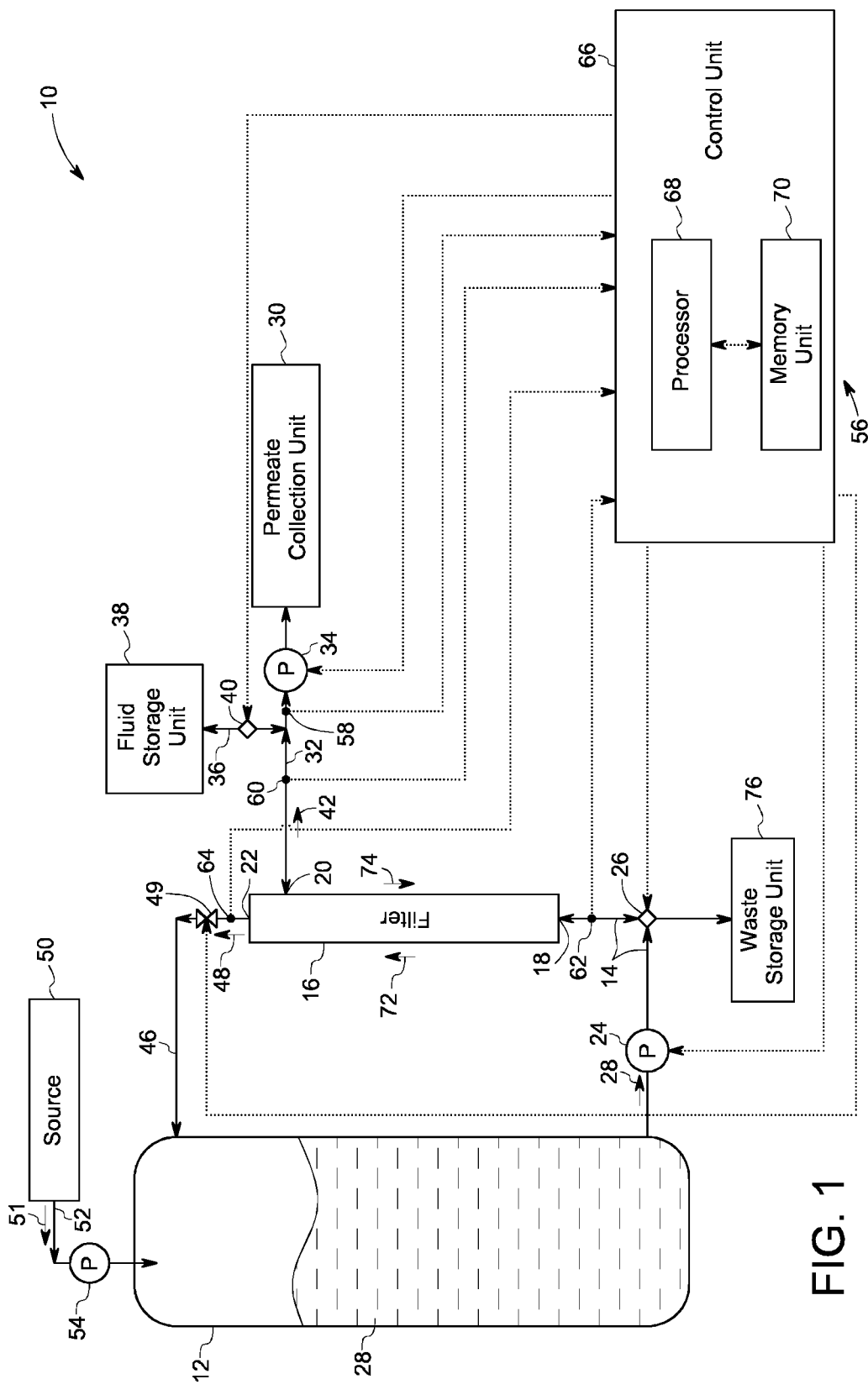
FIG. 1 is a block diagram of a system which utilizes a reverse flow of a permeate fluid through a tangential flow filter in accordance with an embodiment of the present specification.

Referring to FIG. 1, a block diagram of a system 10 in accordance with an embodiment of the present specification is shown. In the illustrated embodiment, the system 10 includes a bioreactor 12 coupled via a feed flow path 14 to a tangential flow filter (for example, hollow fiber filter) 16. The tangential flow filter 16 has an inlet 18, a first outlet 20, and a second outlet 22.

The system 10 further includes a feed pump 24 and a feed control valve 26 coupled to the feed flow path 14. The feed pump 24 is located upstream of the feed control valve 26. The bioreactor 12 is used for storage of a feed fluid 28 associated with cell culture, for example. Specifically, the feed pump 24 is used for feeding the feed fluid 28 at a predetermined flow rate from the bioreactor 12 to the inlet 18 of the tangential flow filter 16 via the feed flow path 14.

The feed control valve 26 is used for controlling a flow of the feed fluid 28 via the feed flow path 14.

Additionally, the system 10 includes a permeate collection unit 30 coupled to the first outlet 20 via a permeate flow path 32. The system 10 also includes a permeate pump 34 coupled to the permeate flow path 32. Further, the system 10 includes a diversion path 36 extending from the permeate flow path 32, at a location upstream of the permeate pump 34, to a fluid storage unit 38. Also, the system 10 includes a permeate control valve (also referred to alternatively as a first permeate control valve) 40 coupled to the diversion path 36. The tangential flow filter 16 is used for separating a permeate fluid 42 from the feed fluid 28 by utilizing a pressure difference across the tangential flow filter 16. The permeate pump 34 is used to feed a first predetermined quantity of the permeate fluid 42 at a predetermined flow rate to the permeate collection unit 30 via the permeate flow path 32. The permeate control valve 40 is used for controlling a flow of a portion of the permeate fluid 42 through the diversion path 36 to the fluid storage unit 38.

Further, the bioreactor 12 is coupled to the second outlet 22 of the tangential flow filter 16 via a retentate flow path 46. A retentate fluid 48 flows via the second outlet 22 of the tangential flow filter 16 and through the retentate flow path 46 to the bioreactor 12. The retentate fluid 48 is a remaining portion of the feed fluid 28 after separation of the permeate fluid 42. A retentate valve 49 is coupled to the retentate flow path 46 and used to control flow of the retentate fluid 48 through the retentate flow path 46. Furthermore, a source 50 is coupled via a flow path 52 to the bioreactor 12. The source 50 is used for storage of a nutrient fluid 51. A transfer pump 54 is coupled to the flow path 52 and used to transfer the nutrient fluid 51 from the source 50 to the bioreactor 12 via the flow path 52. Whenever there is a requirement, the transfer pump 54 is operated to replenish the bioreactor 12 with the nutrient fluid 51. It should be noted herein that the illustrated system 10 is an exemplary embodiment and should not be construed as a limitation. The configuration of the system 10 may vary depending upon the application. The feed pump 24 and the feed control valve 26 are referred to as feed flow control devices, the permeate control valve 40 and the permeate pump 34 are referred to as permeate flow control devices, and the retentate valve 49 is referred to as a retentate flow control device of the system 10.

In another embodiment, instead of using the feed pump 24, a pressurized gas may be fed from a gas source to the bioreactor 12 via a filter for feeding the feed fluid 28 from the bioreactor 12 to the tangential flow filter 16 via the feed flow path 14. In such an embodiment, the permeate pump 34 may not be required.

In the illustrated embodiment, the system 10 further includes a control system 56 having a flow sensor 58 and a first pressure sensor 60 coupled to the permeate flow path 32. The flow sensor 58 is located downstream of the permeate control valve 40 and upstream of the permeate pump 34. The first pressure sensor 60 is located upstream of the permeate control valve 40. The flow sensor 58 is used to measure a flow rate of the permeate fluid 42 exiting the tangential flow filter 16 to the permeate flow path 32. In one embodiment, the flow sensor 58 may output a signal representative of the flow rate of the permeate fluid 42 flowing through the permeate flow path 32. In another embodiment, the flow senor 58 may output a signal representative of a parameter, for example, volume or velocity, of the permeate fluid 42 for computing the flow rate of the permeate fluid 42. In another embodiment, the flow sensor 58 may be disposed downstream of the permeate pump 34. Any type of flow sensor which may be used for measuring the flow rate of the permeate fluid 42 is envisioned. The first pressure sensor 60 is used to sense a pressure of the permeate fluid 42 flowing through the permeate flow path 32.

In another embodiment, the control system 56 may have a flow sensor (not shown) coupled to the feed flow path 14. Such a flow sensor may be used to measure a flow rate of the feed fluid 28 flowing through the feed flow path 14.

The control system 56 further includes a second pressure sensor 62 coupled to the feed flow path 14. The second pressure sensor 62 is located downstream of the feed control valve 26. The second pressure sensor 62 is used to sense a pressure of the feed fluid 28 flowing through the feed flow path 14. The control system 56 additionally includes a third pressure sensor 64 coupled to the retentate flow path 46. The third pressure sensor 64 is used to sense a pressure of the retentate fluid 48 flowing through the retentate flow path 46.

Further, in the illustrated embodiment, the control system 56 includes a control unit 66 having a processor 68 and a memory unit 70 coupled to the processor 68. In some embodiments, the control unit 66 is used to control at least one function of the system 10. In certain embodiments, the control unit 66 may include more than one processor co-operatively working with each other for performing intended functionalities. The control unit 66 is further configured to store and retrieve contents into and from the memory unit 70. In one embodiment, the control unit 66 is configured to initiate and control the functionality of the system 10.

In one embodiment, the control unit 66 includes at least one of a general-purpose computer, a graphics processing unit (GPU), a digital signal processor, and a controller. In other embodiments, the control unit 66 includes a customized processor element such as, but not limited to, an application-specific integrated circuit (ASIC) and a field-programmable gate array (FPGA). In some embodiments, the control unit 66 may be communicatively coupled with at least one of a keyboard, a mouse, and any other input device and configured to receive commands and/or parameters from an operator via a console.

In one embodiment, the memory unit 70 is a random-access memory (RAM), a read only memory (ROM), a flash memory, or any other type of computer readable memory accessible by the processor 68. Also, in certain embodiments, the memory unit 70 may be a non-transitory computer readable medium encoded with a program having a plurality of instructions to instruct the processor 68 to perform a sequence of steps to operate system 10.

In the illustrated embodiment, the control unit 66 is communicatively coupled to the flow sensor 58. In one embodiment, the control unit 66 is configured to receive the output signal representative of the flow rate of the permeate fluid 42 from the flow sensor 58. In another embodiment, the control unit 66 is configured to receive the output signal representative of a parameter, for example, volume or velocity, of the permeate fluid 42 from the flow sensor 58 for computing the flow rate of the permeate fluid 42 in accordance with a known technique.

The control unit 66 is also coupled to the feed pump 24 and the permeate pump 34 and configured to control operations of the feed pump 24 and the permeate pump 34. The control unit 66 may also be coupled to the transfer pump 54 and configured to control the transfer pump 54. The control unit 66 is further coupled to the feed control valve 26, the permeate control valve 40, and the retentate valve 49 and configured to control the actuations of the feed control valve 26, the permeate control valve 40, and the retentate valve 49. Additionally, the control unit 66 is communicatively coupled to the first pressure sensor 60, the second pressure sensor 62, and the third pressure sensor 64. In one embodiment, the control unit 66 is communicatively coupled to the first, second, and third pressure sensors 60, 62, 64 and configured to determine a Trans-Membrane Pressure (TMP) of the tangential flow filter 16 based on outputs from the first, second, and third pressure sensors 60, 62, 64. It should be noted herein that the TMP is representative of a pressure that is needed to pass water through a filter. In another embodiment, the control unit 66 is configured to determine a pressure difference across the tangential flow filter 16 based outputs from the second and third pressure sensors 62, 64.

During an operation of the system 10, the control unit 66 operates the feed pump 24 and controls the feed control valve 26 to feed a first quantity of the feed fluid 28 along a first direction 72 from the bioreactor 12 to the tangential flow filter 16 via the feed flow path 14. The tangential flow filter 16 separates the first quantity of the feed fluid 28 into the permeate fluid 42 and the retentate fluid 48. Specifically, the first quantity of the feed fluid 28 is passed tangentially across the tangential flow filter 16 at positive pressure relative to a permeate side of the tangential flow filter 16. The control unit 66 operates the permeate pump 34 and the permeate flow control valve 40 to feed a first predetermined quantity of the permeate fluid 42 to the permeate collection unit 30 via the permeate flow path 32. The control unit 66 opens the retentate valve 49 to feed the retentate fluid 48 through the retentate flow path 46 to the bioreactor 12.

During certain instances, the control unit 66 stops the permeate pump 34 and opens the permeate control valve 40 to direct a portion of the permeate fluid 42 to the fluid storage unit 38 via the diversion path 36. The control unit 66 determines a time required to fill a quantity of the portion of the permeate fluid 42 in the fluid storage unit 38 based on the determined flow rate of the permeate fluid 42 and a volume of the fluid storage unit 38. As noted earlier, the control unit 66 determines the flow rate of the permeate fluid 42 based on the output of the flow sensor 58.

Thereafter, the control unit 66 closes the permeate control valve 40 and stops the feed pump 24 to stop the flow of the first quantity of the feed fluid 28 along the first direction 72 from the bioreactor 12 via the tangential flow filter 16. Thereafter, the control unit 66 controls the feed control valve 26, opens the permeate control valve 40, and closes the retentate valve 49 to direct the portion of the permeate fluid 42 under gravity along a second direction 74 opposite to the first direction 72 from the fluid storage unit 38 to a waste storage unit 76 via the tangential flow filter 16 for a predefined duration to clean the tangential flow filter 16. The predetermined duration to clean the tangential flow filter 16 may vary depending on the application. In one embodiment, the cleaning of the tangential flow filter 16 is performed at predetermined intervals of time. In one embodiment, the control unit 66 may be used to determine the predetermined intervals of time based on an output of the flow sensor coupled to the feed flow path 14. Here again, the predetermined intervals of time may vary depending on the application.

In one embodiment, the cleaning of the tangential flow filter 16 is performed based on the TMP of the tangential flow filter 16 determined by the control unit 66 based on outputs from the first, second, and third pressure sensors 60, 62, 64. TMP is calculated by the control unit 66 based on the following relation:

$$TMP = ((p_2 + p_3)/2) - p_1$$

where $p_1$ is an output of the first pressure sensor 60, $p_2$ is an output of the second pressure sensor 62, $p_3$ is an output of the third pressure sensor 64. If the TMP is greater is greater than a threshold limit, the control unit 66 determines clogging of the tangential flow filter 16 and the cleaning process is performed as discussed above.

In another embodiment, the cleaning of the tangential flow filter 16 is performed based on a pressure difference across the tangential flow filter 16 determined by the control unit 66 based outputs from the second and third pressure sensors 62, 64. If the pressure difference across the tangential flow filter 16 is greater than a threshold limit, the control unit 66 determines clogging of the tangential flow filter 16 and the cleaning process is performed as discussed above.

In yet another embodiment, the cleaning of the tangential flow filter 16 is performed based on a permeate flux rate of the tangential flow filter 16. The control unit 66 is configured to determine the permeate flux rate of the tangential flow filter 16 based on the measured flow rate of the permeate fluid 42. It should be noted herein that the permeate flux rate of the tangential flow filter 16 is defined as the measured flow rate of the permeate fluid 42 per unit area of the tangential flow filter 16. Specifically, if there is a drop in the permeate flux rate, cleaning of the tangential flow filter 16 is performed.

In yet another embodiment, cleaning of the tangential flow filter 16 is performed based on the detected pressure of the permeate fluid 42. Specifically, if there is a drop in the detected pressure of the permeate fluid 42, cleaning of the tangential flow filter 16 is performed.

After cleaning the tangential flow filter 16, the control unit 66 switches the system 10 from the cleaning state to normal flow state. The volume of the permeate fluid 42 used for cleaning the tangential flow filter 16 and a pressure for reverse flow of the permeate fluid 42 through the tangential flow filter 16 can be controlled based on a type of the tangential flow filter 16 and a density of the feed fluid 28.

Figure 2:
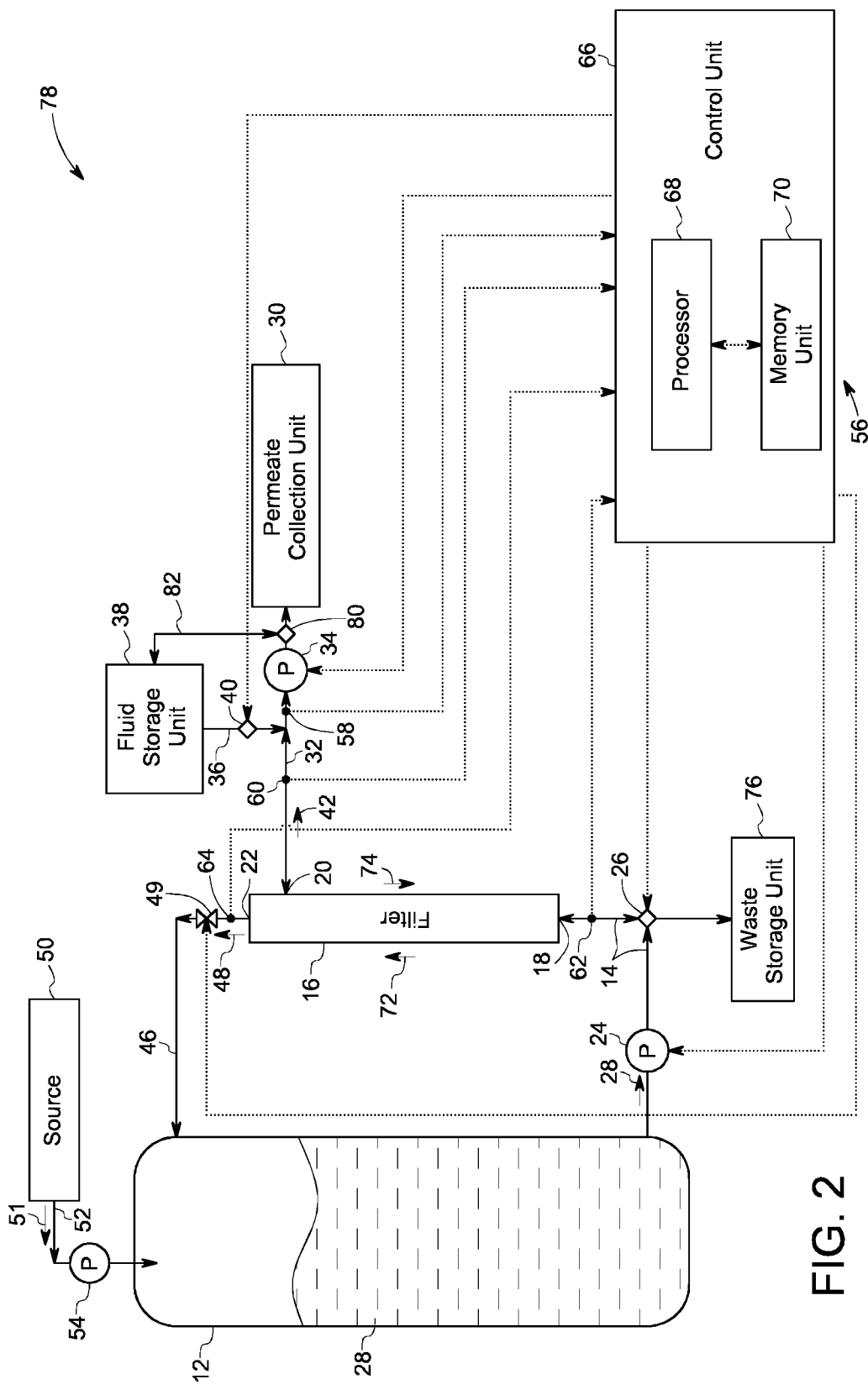
FIG. 2 is a block diagram of a system which utilizes a reverse flow of a permeate fluid through a tangential flow filter in accordance with another embodiment of the present specification.

Referring to FIG. 2, a block diagram of a system 78 in accordance with another embodiment of the present specification is shown. The system 78 is substantially similar to the system 10 shown in FIG. 1. Similar to the system 10, in the illustrated embodiment, the system 78 includes the permeate collection unit 30 coupled to the first outlet 20 via the permeate flow path 32. The system 78 also includes the permeate pump 34 coupled to the permeate flow path 32. Further, the system 78 includes the diversion path 36 extending from the permeate flow path 32, at the location upstream of the permeate pump 34, to the fluid storage unit 38. Also, the system 78 includes the first permeate control valve 40 coupled to the diversion path 36. Specifically, the first permeate control valve 40 is located downstream of the fluid storage unit 38. The system 78 also includes a second permeate control valve 80 coupled to the permeate flow path 32 and located downstream of the permeate pump 34 and upstream of the fluid storage unit 38. The feed pump 24 and the feed control valve 26 are referred to as feed flow control devices, the first and second permeate control valves 40, 80 and the permeate pump 34 are referred to as permeate flow control devices, and the retentate valve 49 is referred to as retentate flow control device of the system 78.

The permeate pump 34 is used to feed a first predetermined quantity of the permeate fluid 42 at a predetermined flow rate to the permeate collection unit 30 via the permeate flow path 32. In the illustrated embodiment, the first permeate control valve 40 is used for controlling the flow of the portion of the permeate fluid 42 from the fluid storage unit 38 to the permeate flow path 32 via the diversion path 36.

The second permeate control valve 80 is used for controlling flow of the first predetermined quantity of the permeate fluid 42 at the predetermined pressure to the permeate collection unit 30 via the permeate flow path 32. Further, the second permeate control valve 80 is also used to control the flow of the portion of the permeate fluid 42 to the fluid storage unit 38 via a path 82. In the illustrated embodiment, the control unit 66 is also coupled to the first and second permeate control valves 40, 80 and configured to control the actuations of the first and second permeate control valves 40, 80.

During an operation of the system 78, the control unit 66 operates the feed pump 24 and controls the feed control valve 26 to feed a first quantity of the feed fluid 28 along the first direction 72 from the bioreactor 12 to the tangential flow filter 16 via the feed flow path 14. The tangential flow filter 16 separates the first quantity of the feed fluid 28 into the permeate fluid 42 and the retentate fluid 48. Then, the control unit 66 closes the first permeate control valve 40, controls the second permeate control valve 80, and operates the permeate pump 34 to feed the first predetermined quantity of the permeate fluid 42 to the permeate collection unit 30 via the permeate flow path 32. The control unit 66 opens the retentate valve 49 to direct the retentate fluid 48 via the retentate flow path 46 to the bioreactor 12. During certain instances, the control unit 66 controls the second permeate control valve 80 to direct a portion of the permeate fluid 42 to the fluid storage unit 38 via the path 82. As noted earlier, the control unit 66 determines a time required to fill a quantity of the portion of the permeate fluid 42 in the fluid storage unit 38 based on the determined flow rate of the permeate fluid 42 and a volume of the fluid storage unit 38. The control unit 66 determines the flow rate of the permeate fluid 42 based on the output of the flow sensor 58.

Thereafter, the control unit 66 stops the feed pump 24 to stop the flow of the first quantity of the feed fluid 28 along the first direction 72 from the bioreactor 16 via the tangential flow filter 16. Thereafter, the control unit 66 stops the permeate pump 34, controls the feed control valve 26, closes the retentate valve 49, and opens the first permeate control valve 40 to direct the portion of the permeate fluid 42 under gravity along the second direction 74 opposite to the first direction 72 from the fluid storage unit 38 to the waste storage unit 76 via the diversion path 36, the permeate flow path 32, and the tangential flow filter 16 for a predefined duration to clean the tangential flow filter 16. The predetermined duration to clean the tangential flow filter 16 may vary depending on the application.

In another embodiment, the control unit 66 controls the feed control valve 26, closes the first permeate control valve 40 and the retentate valve 49, controls the second permeate control valve 80, and changes a direction of rotation of the permeate pump 34 to direct the portion of the permeate fluid 42 along the second direction 74 opposite to the first direction 72 from the fluid storage unit 38 to the waste storage unit 76 via the path 82, the permeate flow path 32, and the tangential flow filter 16 for a predefined duration to clean the tangential flow filter 16. After cleaning the tangential flow filter 16, the control unit 66 switches the system 78 from the cleaning state to normal flow state.

Figure 3:
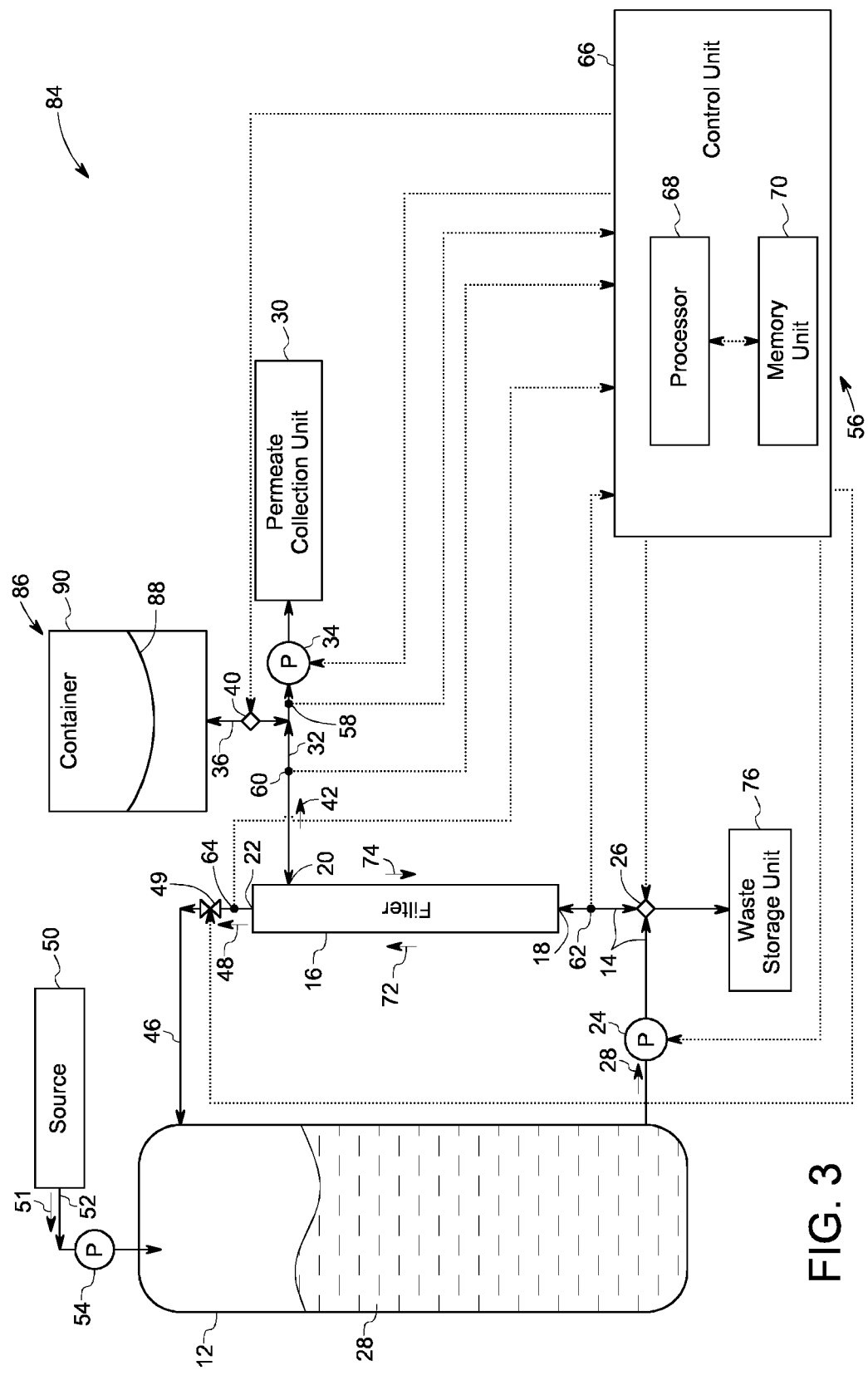
FIG. 3 is a block diagram of a system including a fluid storage unit having a diaphragm disposed in a container in accordance with an embodiment of the present specification.

Referring to FIG. 3, a block diagram of a system 84 in accordance with an embodiment of the present specification is shown. The system 84 is substantially similar to the system 10 discussed with reference to FIG. 1. In the illustrated embodiment, the system 84 includes the permeate collection unit 30 coupled to the first outlet 20 via the permeate flow path 32. The system 84 includes the permeate pump 34 coupled to the permeate flow path 32. Further, the system 84 includes the diversion path 36 extending from the permeate flow path 32, at a location upstream of the permeate pump 34, to a fluid storage unit 86. The pump storage unit 86 includes a diaphragm 88 disposed within a container 90. The diaphragm 88 may be made of a material including at least one of but not limited to rubber (such as neoprene, buna-N, ethylene propylene diene monomer rubber, or the like), thermoplastic elastomer (such as Saniflex®, Wilflex™, polyurethane, Geolast™, or the like), and polytetrafluoroethylene. Also, the system 78 includes the permeate control valve 40 coupled to the diversion path 36. The permeate pump 34 is used to feed a first predetermined quantity of the permeate fluid 42 at a predetermined flow rate to the permeate collection unit 30 via the permeate flow path 32. The permeate control valve 40 is used for controlling a flow of a portion of the permeate fluid 42 flowing through the diversion path 36 to the fluid storage unit 86.

In the illustrated embodiment, the control unit 66 is also coupled to an actuator (not shown) used to actuate the diaphragm 88 disposed within the container 90. As noted earlier, during certain instances, the control unit 66 stops the permeate pump 34 and opens the permeate control valve 40 to direct a portion of the permeate fluid 42 to the fluid storage unit 86 via the diversion path 36. The control unit 66 opens the retentate valve 49 to direct the retentate fluid 48 via the retentate flow path 46 to the bioreactor 12. Thereafter, the control unit 66 controls the feed control valve 26, closes the retentate valve 49, opens the permeate control valve 40, and actuates the diaphragm 88 to direct the portion of the permeate fluid 42 along the second direction 74 opposite to the first direction 72 from the fluid storage unit 86 to the waste storage unit 76 via the permeate flow path 32 and the tangential flow filter 16 for a predefined duration to clean the tangential flow filter 16.

Figure 4:
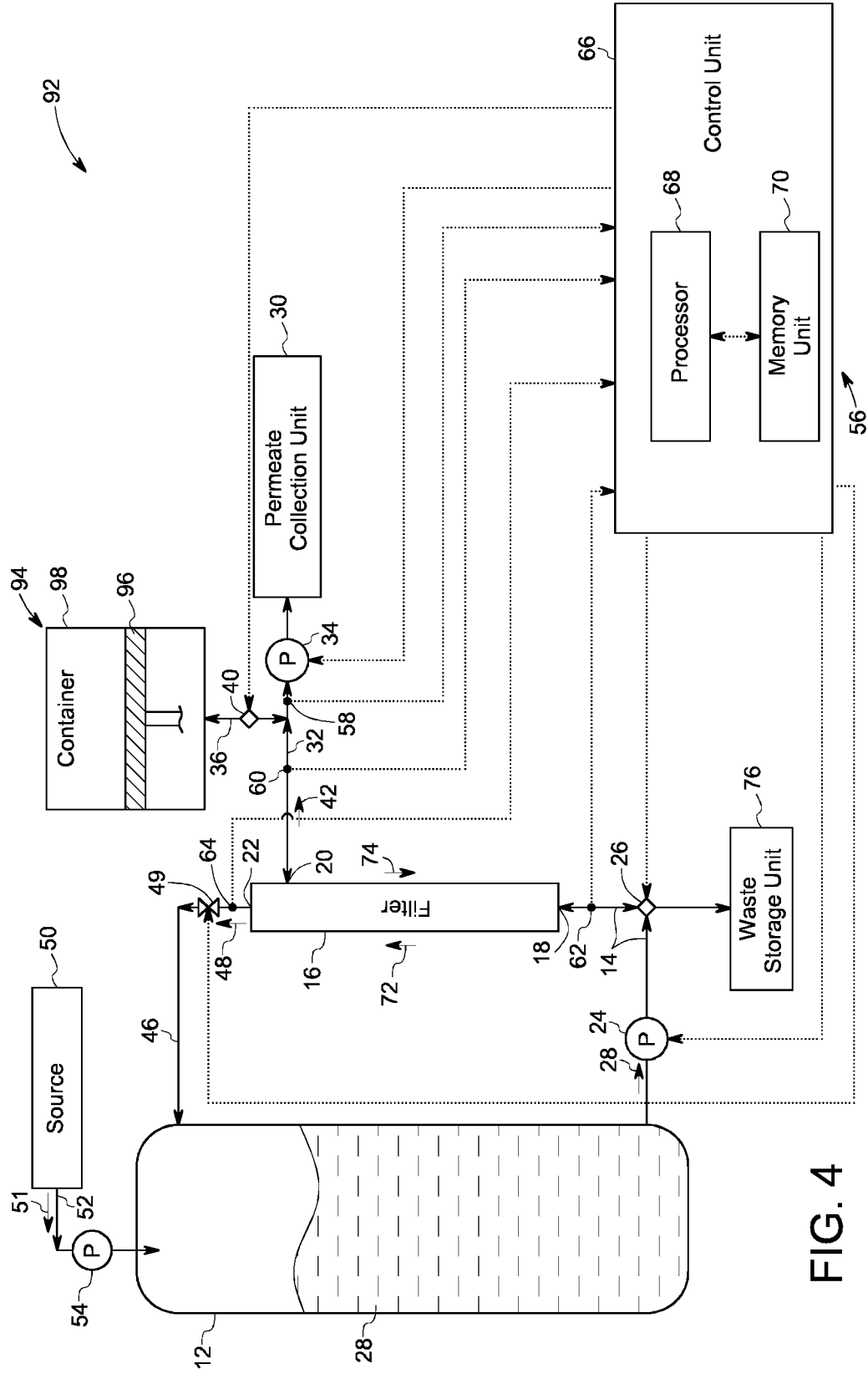
FIG. 4 is a block diagram of a system including a fluid storage unit having a piston disposed in a container in accordance with an embodiment of the present specification.

Referring to FIG. 4, a block diagram of a system 92 in accordance with an embodiment of the present specification is shown. The system 92 is substantially similar to the system 10 discussed with reference to FIG. 1. In the illustrated embodiment, the system 92 includes the permeate collection unit 30 coupled to the first outlet 20 via the permeate flow path 32. The system 92 includes the permeate pump 34 coupled to the permeate flow path 32. Further, the system 92 includes the diversion path 36 extending from the permeate flow path 32, at a location upstream of the permeate pump 34, to a fluid storage unit 94. The fluid storage unit 94 includes a piston 96 disposed within a container 98. Also, the system 94 includes the permeate control valve 40 coupled to the diversion path 36. The permeate pump 34 is used to feed a first predetermined quantity of the permeate fluid 42 at a predetermined flow rate to the permeate collection unit 30 via the permeate flow path 32. The permeate control valve 40 is coupled to the diversion path 36 and used for controlling a flow of a portion of the permeate fluid 42 flowing through the diversion path 36 to the fluid storage unit 94.

In the illustrated embodiment, the control unit 66 is also coupled to an actuator (not shown) used to actuate the piston 96 disposed within the container 98. As noted earlier, during certain instances, the control unit 66 stops the permeate pump 34 and opens the permeate control valve 40 to direct a portion of the permeate fluid 42 to the fluid storage unit 94 via the diversion path 36. The control unit 66 opens the retentate valve 49 to direct the retentate fluid 48 via the retentate flow path 46 to the bioreactor 12. Thereafter, the control unit 66 controls the feed control valve 26, closes the retentate valve 49, opens the permeate control valve 40, and actuates the piston 96 to direct the portion of the permeate fluid 42 along the second direction 74 opposite to the first direction 72 from the fluid storage unit 94 to the waste storage unit 76 via the permeate flow path 32 and the tangential flow filter 16 for a predefined duration to clean the tangential flow filter 16.

With reference to FIGS. 1-4, in certain embodiments, the fluid storage units 38, 86, 94, the diversion path 36, the first and second permeate flow control valves 40, 80 and path 82 may not be required. In such embodiments, the control unit 66 controls the permeate pump 34 to rotate along an opposite direction to direct the portion of the permeate fluid 42 along the second direction 74 opposite to the first direction 72 from the permeate collection unit 30 to the waste storage unit 76 via the permeate flow path 32, the tangential flow filter 16, and the feed flow path 14 for a predefined duration to clean the tangential flow filter 16.

In certain other embodiments, instead of the permeate fluid 42, the fluid storage units 38, 86, 94 may be filled with the nutrient fluid 51 from a source, such as the source 50 or an external source. In such embodiments, a portion of the nutrient fluid 51 is directed along the second direction 74 opposite to the first direction 72 from the fluid storage units 38, 86, 94 to the waste storage unit 76 via the permeate flow path 32, the tangential flow filter 16, and the feed flow path 14 for a predefined duration to clean the tangential flow filter 16.

Figure 5:
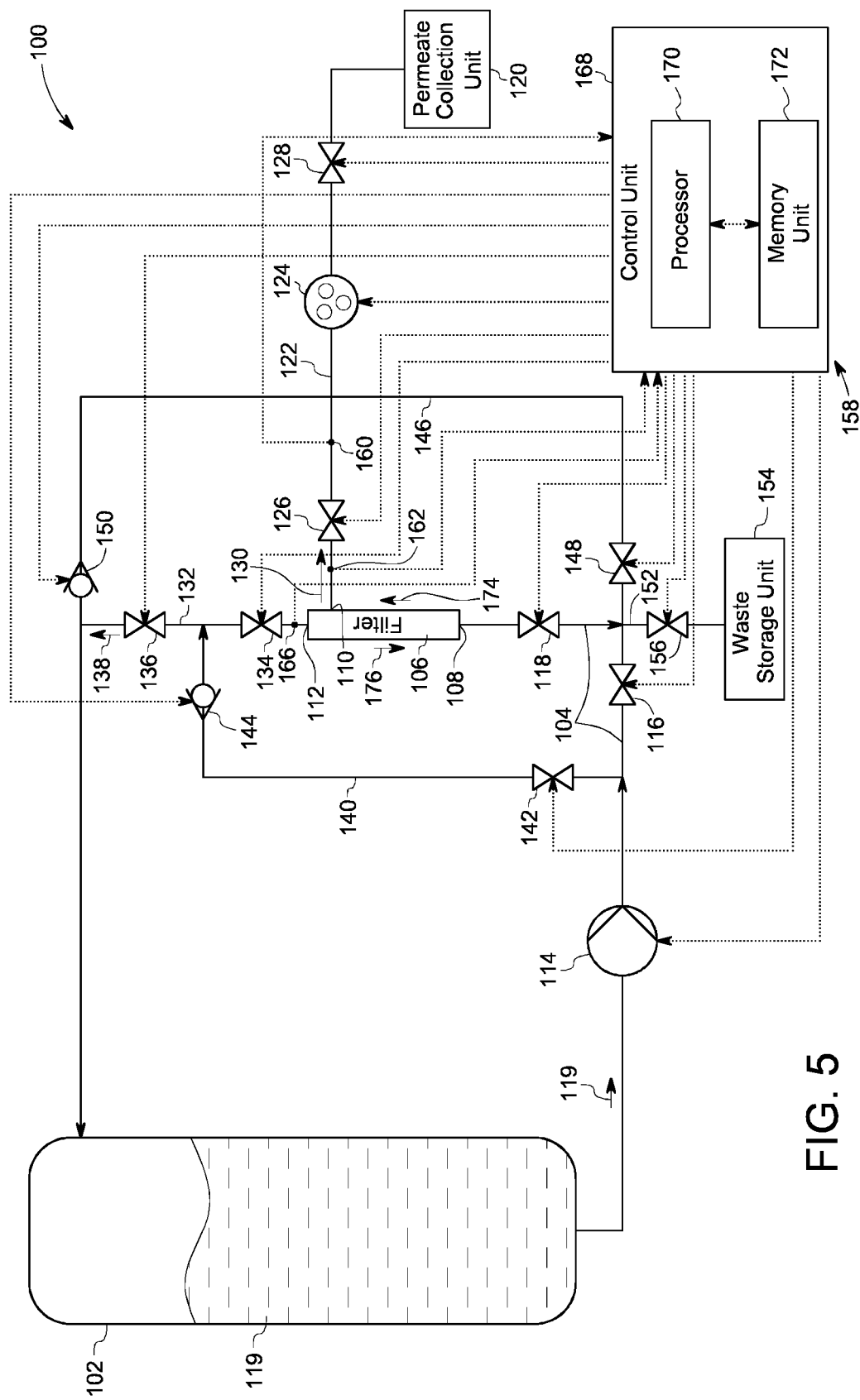
FIG. 5 is a block diagram of a system which utilizes a reverse flow of a feed fluid through a tangential flow filter in accordance with an embodiment of the present specification.

Referring to FIG. 5, a block diagram of a system 100 in accordance with an embodiment of the present specification is shown. In the illustrated embodiment, the system 100 includes a bioreactor 102 coupled via a feed flow path 104 to a tangential flow filter 106. The tangential flow filter 106 has an inlet 108, a first outlet 110, and a second outlet 112.

The system 100 further includes a feed pump 114, a first feed control valve 116, and a second feed control valve 118 coupled to the feed flow path 104. The feed pump 114 is located upstream of the first feed control valve 116 and the second feed control valve 118 is located downstream of the first feed control valve 116. The bioreactor 102 is used for storage of a feed fluid 119 associated with cell culture, for example. Specifically, the feed pump 114 is used for feeding the feed fluid 119 at a predetermined flow rate from the bioreactor 102 to the inlet 108 of the tangential flow filter 106 via the feed flow path 104. The first and second feed control valves 114, 116 are used for controlling a flow of the feed fluid 119 via the feed flow path 104.

Additionally, the system 100 includes a permeate collection unit 120 coupled to the first outlet 110 via a permeate flow path 122. The system 100 also includes a permeate pump 124, a first permeate control valve 126, and a second permeate control valve 128 coupled to the permeate flow path 122. The permeate pump 124 is located downstream of the first permeate control valve 126 and the second permeate control valve 128 is located downstream of the permeate pump 124. The tangential flow filter 106 is used for separating a permeate fluid 130 from the feed fluid 119 by utilizing a pressure difference across the tangential flow filter 106. The permeate pump 124 is used to feed the permeate fluid 130 at a predetermined flow rate to the permeate collection unit 120 via the permeate flow path 122. The first and second permeate control valves 126, 128 are used for controlling a flow of the permeate fluid 130 flowing through the permeate flow path 122 to the permeate collection unit 120.

Further, the bioreactor 102 is coupled to the second outlet 112 of the tangential flow filter 106 via a retentate flow path 132. The system 100 also includes a first retentate control valve 134 and a second retentate control valve 136 coupled to the retentate flow path 132. A retentate fluid 138 flows via the second outlet 112 of the tangential flow filter 106 and through the retentate flow path 132 to the bioreactor 102. The retentate fluid 138 is a remaining portion of the feed fluid 119 after separation of the permeate fluid 130. The first and second retentate control valves 134, 136 are used for controlling the flow of the retentate fluid 134 via the retentate flow path 132 to the bioreactor 102.

In the illustrated embodiment, the system 100 includes a feed bypass path 140 extending from the feed flow path 104, at a location downstream of the feed pump 114, to the retentate flow path 132, at a location downstream of the first retentate control valve 134 and upstream of the second retentate control valve 136. A third feed control valve 142 and a first non-return valve 144 are coupled to the feed bypass path 140. The first non-return valve 144 is disposed downstream of the third feed control valve 142. The system 100 also includes a return path 146 extending from the feed flow path 104, at a location between the first and second feed control valves 116, 118, to the retentate flow path 132, at a location downstream of the second retentate control valve 136. A fourth feed control valve 148 and a second non-return valve 150 are coupled to the return path 146. The second non-return valve 150 is disposed downstream of the fourth feed control valve 148.

The system 100 further includes a waste path 152 extending from a location intersecting the feed flow path 104 and the return path 146 to a waste storage unit 154. A waste control valve 156 is coupled to the waste path 152. The feed pump 114, the first, second, third, and fourth feed control valves 116, 118, 142, 148, the first and second non-return valves 144, 150, and the waste control valve 156 are referred to as feed flow control devices, the permeate pump 124 and the first and second permeate control valves 126, 128 are referred to as permeate flow control devices, and the first and second retentate control valves 134, 136 are referred to as retentate flow control devices. In one embodiment, the first, second, third, and fourth feed control valves 116, 118, 142, 148, the first and second permeate control valves 126, 128, the first and second retentate control valves 134, and the waste control valve 156 are pinch valves. The configuration of the system 100 may vary depending upon the application.

In another embodiment, instead of using the feed pump 114, a pressurized gas may be fed from a gas source to the bioreactor 102 via a filter for feeding the feed fluid 119 from the bioreactor 102 to the tangential flow filter 106 via the feed flow path 104. In such an embodiment, the permeate pump 124 may not be required.

In the illustrated embodiment, the system 100 further includes a control system 158 having a flow sensor 160 and a first pressure sensor 162 coupled to the permeate flow path 122. The flow sensor 160 is located downstream of the first permeate control valve 126 and upstream of the permeate pump 124. The first pressure sensor 162 is located upstream of the first permeate control valve 126. In another embodiment, the flow sensor 160 is disposed downstream of the permeate pump 124. The flow sensor 160 is used to measure a flow rate of the permeate fluid 130 flowing through the tangential flow filter 106 to the permeate flow path 122. The first pressure sensor 162 is used to sense a pressure of the permeate fluid 130 flowing through the permeate flow path 122.

In another embodiment, the control system 158 may have a flow sensor (not shown) coupled to the feed flow path 104. Such a flow sensor may be used to measure a flow rate of the feed fluid 119 flowing through the feed flow path 104.

The control system 158 further includes a second pressure sensor 164 coupled to the feed flow path 104. The second pressure sensor 164 is located downstream of the first feed control valve 116. The second pressure sensor 164 is used to sense a pressure of the feed fluid 119 flowing through the feed flow path 104. The control system 158 additionally includes a third pressure sensor 166 coupled to the retentate flow path 132. The third pressure sensor 166 is used to sense a pressure of the retentate fluid 138 flowing through the retentate flow path 132.

Further, in the illustrated embodiment, the control system 158 includes a control unit 168 having a processor 170 and a memory unit 172 coupled to the processor 170. In some embodiments, the control unit 168 is used to control at least one function of the system 100. The control system 158 is similar to the control system 56 shown in FIG. 1.

In the illustrated embodiment, the control unit 168 is communicatively coupled to the flow sensor 160. In one embodiment, the control unit 168 is configured to receive the output signal representative of the flow rate of the permeate fluid 130 from the flow sensor 160. In another embodiment, the control unit 168 is configured to receive the output signal representative of a parameter, for example, volume or velocity, of the permeate fluid 130 from the flow sensor 160 for computing the flow rate of the permeate fluid 130 in accordance with a known technique.

The control unit 168 is also coupled to the feed pump 114 and the permeate pump 124 and configured to control operation of the feed pump 114 and the permeate pump 124. The control unit 168 is further coupled to and configured to control the first, second, third, and fourth feed control valves 116, 118, 142, 148, the first and second permeate control valves 126, 128, the first and second retentate control valves 134, 136, the first and second non-return valves 144, 150, and the waste control valve 156. Additionally, the control unit 168 is communicatively coupled to the first pressure sensor 162, the second pressure sensor 164, and the third pressure sensor 166. In one embodiment, the control unit 168 is communicatively coupled to the first, second, and third pressure sensors 162, 164, 166 and configured to determine a Trans-Membrane Pressure (TMP) of the tangential flow filter 106 based on outputs from the first, second, and third pressure sensors 162, 164, 166. In another embodiment, the control unit 168 is configured to determine a pressure difference across the tangential flow filter 106 based outputs from the second and third pressure sensors 164, 166.

During an operation of the system 100, the control unit 168 operates the feed pump 114 and controls the first and second feed control valve 116, 118 to feed a first quantity of the feed fluid 119 along a first direction 174 from the bioreactor 102 to the tangential flow filter 106 via the feed flow path 104. The tangential flow filter 106 separates the first quantity of the feed fluid 119 into the permeate fluid 130 and the retentate fluid 134. The control unit 168 operates the permeate pump 124 to feed the permeate fluid 130 to the permeate collection unit 120 via the permeate flow path 122. The control unit 168 opens the retentate fluid 134 to feed the retentate fluid 134 via the retentate flow path 132 to the bioreactor 102.

During certain instances, the control unit 168 closes the first and second permeate control valves 126, 128 and stops the permeate pump 124 to stop the flow of the flow of the permeate fluid 130 to the permeate collection unit 120. The control unit 168 also closes the first and second feed control valves 116, 118, the second retentate control valve 136 and the waste control valve 156 to direct a second quantity of the feed fluid 119 along a second direction 176 opposite to the first direction 174 from the feed flow path 104 via the feed bypass path 140, the retentate flow path 132, and the tangential flow filter 106 for a predefined duration to clean the tangential flow filter 106. The predetermined duration to clean the tangential flow filter 106 may vary depending on the application. In one embodiment, the cleaning of the tangential flow filter 106 is performed at predetermined intervals of time.

In one embodiment, the cleaning of the tangential flow filter 106 is performed based on the TMP of the tangential flow filter 106 determined by the control unit 168 based on outputs from the first, second, and third pressure sensors 162, 164, 166. If the TMP is greater than a threshold limit, the control unit 168 determines clogging of the tangential flow filter 106 and the cleaning process is performed as discussed above. In another embodiment, the cleaning of the tangential flow filter 106 is performed based on a pressure difference across the tangential flow filter 106 determined by the control unit 168 based outputs from the second and third pressure sensors 164, 166. If the pressure difference across the tangential flow filter 106 is greater than a threshold limit, the control unit 168 determines clogging of the tangential flow filter 106 and the cleaning process is performed as discussed above.

In yet another embodiment, the cleaning of the tangential flow filter 106 is performed based on a permeate flux rate of the tangential flow filter 106. The control unit 168 is configured to determine the permeate flux rate of the tangential flow filter 106 based on the measured flow rate of the permeate fluid 130. Specifically, if there is a drop in the permeate flux rate, cleaning of the tangential flow filter 106 is performed.

In yet another embodiment, cleaning of the tangential flow filter 106 is performed based on the detected pressure of the permeate fluid 130. Specifically, if there is a drop in the detected pressure of the permeate fluid 130, cleaning of the tangential flow filter 106 is performed.

Thereafter, the second quantity of the feed fluid 119 is fed via the feed flow path 104, the return path 146, and the retentate flow path 132 to the bioreactor 106. In another embodiment, the fourth feed control valve 148 is closed and the waste control valve 156 is opened to direct the second quantity of the feed fluid 119 from the tangential flow filter 106 via the feed flow path 104 and the waste path 152 to the waste storage unit 154.

After cleaning the tangential flow filter 106, the control unit 168 switches the system 100 from the cleaning state to normal flow state. The volume of the permeate fluid 42 used for cleaning the tangential flow filter 16 and a pressure for reverse flow of the permeate fluid 130 through the tangential flow filter 106 can be controlled based on a type of the tangential flow filter 106 and a density of the feed fluid 119.

In accordance with the embodiments of the present specification, the reverse of the feed fluid or the permeate fluid or the nutrient fluid through the tangential flow filter creates a turbulence, thereby reducing clogging of the tangential flow filter. The exemplary techniques enable to extend a life of the single use tangential flow filter and also extend a duration for which the process can be run without interruption. It is possible to achieve higher cell densities because the tangential flow filter can be cleaned in a sterile manner during the process. In some embodiments, all permutations and combinations of FIGS. 1-5 are envisioned.

While only certain features of the specification have been illustrated and described herein, many modifications and changes will occur to those skilled in the art. It is, therefore, to be understood that the appended claims are intended to cover all such modifications and changes as fall within the true spirit of the specification.

The invention claimed is:

1. A method of operation of a perfusion system, the method comprising:

inducing, via at least one feed flow control device, a first quantity of a feed fluid to flow along a first direction from a bioreactor to a tangential flow filter via a feed flow path;

controlling the at least one feed flow control device in the feed flow path, by a control unit, for controlling said flow;

as a result of said flow along said first direction, allowing the tangential flow filter to separate the first quantity of the feed fluid into a permeate fluid and a retentate fluid;

operating the control unit to control the at least one feed flow control device to inhibit or stop the flow of the first quantity of the feed fluid; and operating the control unit to control the at least one feed flow control device to direct a) a further flow of a second quantity of the feed fluid from the bioreactor, b) a portion of the permeate fluid, and c) a portion of a fresh nutrient fluid from a source, along a second direction opposite to the first direction via the tangential flow filter to a waste storage unit for a predefined duration to clean the tangential flow filter.

2. The method as claimed in claim 1, wherein controlling the at least one feed control device comprises controlling a feed pump and a feed control valve.

3. The method as claimed in claim 1, comprising feeding a first predetermined quantity of the permeate fluid to a permeate collection unit via a permeate flow path by operating at least one permeate flow control device, using the control unit.

4. The method as claimed in claim 3, wherein operating the at least one permeate flow control device comprises operating a permeate pump and closing a permeate flow control valve.

5. The method as claimed in claim 4, comprising stopping the permeate pump and opening the permeate control valve, by the control unit, to direct the portion of the permeate fluid to a fluid storage unit via the permeate flow path and a diversion path.

6. The method as claimed in claim 5, comprising determining, by the control unit, a time required to fill a quantity of the portion of the permeate fluid in the fluid storage unit based on a flow rate of the permeate fluid and a volume of the fluid storage unit.

7. The method as claimed in claim 5, comprising closing the permeate control valve, by the control unit, after directing the portion of the permeate fluid to the fluid storage unit.

8. The method as claimed in claim 7, comprising controlling the feed control valve and opening the permeate control valve, by the control unit, to direct the portion of the permeate fluid along the second direction opposite to the first direction from the fluid storage unit to the waste storage unit via the diversion path, the permeate flow path, the tangential flow filter, and the feed flow path.

9. The method as claimed in claim 8, comprising controlling a diaphragm of the fluid storage unit by the control unit to direct the portion of the permeate fluid along the second direction opposite to the first direction from the fluid storage unit to the waste storage unit via the diversion path, the permeate flow path, the tangential flow filter, and the feed flow path.

10. The method as claimed in claim 8, comprising controlling a piston of the fluid storage unit, by the control unit, to direct the portion of the permeate fluid along the second direction opposite to the first direction from the fluid storage unit to the waste storage unit via the diversion path, the permeate flow path, the tangential flow filter, and the feed flow path.

11. The method as claimed in 3, comprising operating the at least one permeate flow control device by:

closing a first permeate control valve located downstream of a fluid storage unit, by the control unit;

controlling a second permeate control valve located downstream of a permeate pump and upstream of the fluid storage unit, by the control unit; and operating the permeate pump by the control unit to direct the portion of the permeate fluid to the fluid storage unit via the permeate flow path.

12. The method as claimed in claim 11, comprising stopping the permeate pump by the control unit after directing the portion of the permeate fluid to the fluid storage unit.

13. The method as claimed in claim 12, comprising controlling the feed control valve and opening the second permeate control valve, by the control unit, to direct the portion of the permeate fluid along the second direction opposite to the first direction from the fluid storage unit to the waste storage unit via a diversion path, the permeate flow path, the tangential flow filter, and the feed flow path.

14. The method as claimed in claim 12, comprising controlling the feed control valve and changing a direction of rotation of the permeate pump, by the control unit, to direct the portion of the permeate fluid along the second direction opposite to the first direction from the fluid storage unit to the waste storage unit via a diversion path, the permeate flow path, the tangential flow filter, and the feed flow path.

15. The method as claimed in claim 1, wherein operating the control unit to control the at least one feed flow control device comprises directing at least one of the further flow of the second quantity of the feed fluid from the bioreactor and the portion of the permeate fluid along the second direction opposite to the first direction via the tangential flow filter for the predefined duration at predetermined intervals of time.

16. The method as claimed in claim 1, wherein operating the control unit comprises directing at least one of the further flow of the second quantity of the feed fluid from the bioreactor and the portion of the permeate fluid along the second direction opposite to the first direction via the tangential flow filter for the predefined duration based on at least one of a determined pressure difference across the tangential flow filter and a determined transmembrane pressure of the tangential flow filter.

* * * * *